(12) United States Patent
Lambert

(10) Patent No.: US 8,874,378 B2
(45) Date of Patent: Oct. 28, 2014

(54) SYSTEM AND METHOD FOR TARGETING RELEVANT RESEARCH ACTIVITY IN RESPONSE TO ANGIOGENIC REGULATOR ANALYSES

(76) Inventor: Rebecca Lambert, Washington, CT (US)

( * ) Notice: Subject to any disclaimer, the term of this patent is extended or adjusted under 35 U.S.C. 154(b) by 850 days.

(21) Appl. No.: 13/051,440

(22) Filed: Mar. 18, 2011

(65) Prior Publication Data

US 2011/0231104 A1  Sep. 22, 2011

Related U.S. Application Data

(60) Provisional application No. 61/315,670, filed on Mar. 19, 2010.

(51) Int. Cl.
*G06F 19/28* (2011.01)
*G06F 19/00* (2011.01)
*G06F 19/18* (2011.01)

(52) U.S. Cl.
CPC .......... *G06F 19/324* (2013.01); *G01N 2800/60* (2013.01); *G06F 19/28* (2013.01); *G06F 19/18* (2013.01)
USPC .......................................................... 702/19

(58) Field of Classification Search
CPC ....... G06F 19/324; G06F 19/18; G06F 19/28; A61L 2300/416
USPC .......................... 702/31, 32; 435/7.92; 436/64
See application file for complete search history.

(56) References Cited

U.S. PATENT DOCUMENTS

| | | | |
|---|---|---|---|
| 7,444,308 B2 | 10/2008 | Guyon et al. | |
| 2003/0233250 A1 | 12/2003 | Joffe et al. | |
| 2005/0069963 A1 | 3/2005 | Lokshin et al. | |
| 2005/0086078 A1 | 4/2005 | Maloney et al. | |
| 2009/0234198 A1 | 9/2009 | Vorse | |
| 2010/0017225 A1 | 1/2010 | Oakley et al. | |
| 2013/0177928 A1* | 7/2013 | Peterson et al. | 435/7.92 |

\* cited by examiner

*Primary Examiner* — Manuel L Barbee
(74) *Attorney, Agent, or Firm* — Preti Flaherty Beliveau & Pachios LLP

(57) ABSTRACT

A system and method for targeting relevant research activity for clinical application in response to angiogenic regulator analyses. An angiogenic analysis is performed on a patient blood sample in order to detect the level of each of at least ten angiogenic regulators. The levels of the tested regulators are used as indexes to identify relevant peer-reviewed research publications from among a large database of articles. The most relevant peer-reviewed literature reporting research and studies that have been conducted to identify, moderate, and define the mechanisms unique to individual and combinations of angiogenic regulators for various disease states are then provided to the patient and/or to the patient's physician, optionally in conjunction with a summarization of the treatment recommendations gleaned from the provided literature. The customized information delivery provides the patient and physician a range of published peer-reviewed therapeutic options and published research studies for moderating the out of range regulators to within normal range or other diagnostic significant range.

32 Claims, 3 Drawing Sheets

SYSTEM AND METHOD FOR TARGETING RELEVANT RESEARCH ACTIVITY IN RESPONSE TO ANGIOGENIC REGULATOR ANALYSES

CROSS REFERENCE TO RELATED APPLICATIONS

This application claims priority under 35 U.S.C. §119(e) of U.S. provisional patent application No. 61/315,670, filed Mar. 19, 2010, entitled System and Method for Targeting Relevant Research Activity in Response to Angiogenic Regulator Analyses, the entire disclosure of which is hereby incorporated by reference.

STATEMENT REGARDING FEDERALLY SPONSORED RESEARCH OR DEVELOPMENT n/a

BACKGROUND OF THE INVENTION

Angiogenesis refers to the growth of new blood vessels, either through sprouting or vessel splitting. It is a condition which exists in health on three occasions: menstruation, pregnancy and wound healing (when capillaries rush to a wound site to heal it and retreat after approximately 10-14 days). However, pathological angiogenesis, the abnormal and rapid development of blood vessels, is associated with and drives many diseases including cancer, psoriasis and age-related macular degeneration. In cancerous tissue, tumors cannot grow or spread (metastasize) without the development of new blood vessels. Blood vessels supply tissues with oxygen and nutrients necessary for survival and growth. Endothelial cells, the cells that form the walls of blood vessels, are the source of new blood vessels.

New vessel growth is tightly controlled by a finely tuned balance between factors that activate endothelial cell growth and those that inhibit it. Over 50 individual endogenous angiogenic regulators have been identified as angiogenic factors. They may be measured in blood, serum, urine, tissue and lymph samples. Regulators are broadly classified as: 1) angiogenic activators, stimulators, or growth factors; and 2) endogenous angiogenic inhibitors (cf. synthetic drugs intended to inhibit angiogenesis). It is the unique relationship between these two types of regulators that determines if angiogenesis occurs and thereby supports disease.

For example, about 50 proteins are currently known to regulate endothelial cell replication, some of which are shown in Table I.

TABLE I

| NAME | FULL NAME |
| --- | --- |
| VEG-F | Vascular Endothelial Growth Factor |
| EGF | Epidermal Growth Factor |
| bFGF-Basic | Fibroblast Growth Factor-Basic |
| IL-2 | Interleukin-2 |
| PDGF-BB | Platelet-derived Growth Factor-BB |
| TNF-α | Tumor Necrosis Factor-alpha |
| IL-1β | Interleukin-1 beta |
| IL-8 | Interleukin-8 |
| IL-10 | Interleukin-10 |
| TSP-1 | Thrombospondin-1 |
| COX-2 | Cyclooxygenace |
| HGF | Hepatocyte Growth Factor |
| IGF-1 | Insulin like Growth Factor |
| MMP-2 | Matrix Metalloproteinase-2 |

TABLE I-continued

| NAME | FULL NAME |
| --- | --- |
| MMP-9 | Matrix Metalloproteinase-9 |
| TNF-β | Tumor Necrosis Factor-beta |
| TGF-β | Transforming Growth Factor-beta |
| Angiogenin | Angiogenin |
| GM-CSF | Granulocyte Macrophage Colony-Stimulating Factor |
| Endostatin | Endostatin (collagen XVIII fragment) |
| Angiostatin | Angiostatin (plasminogen fragment) |
| IL-6 | Interleukin-6 |
| G-CSF | Granulocyte Colony-Stimulating Factor |
| IL-7 | Interleukin-7 |
| Kringle 5 | Kringle 5 (plasminogen fragment) |
| Angiopoitin-1 | Angiopoitin-1 |
| FGA/FGB | Fibrinogin |

At a critical point in the growth of a tumor, the tumor sends out signals to the nearby capillaries to activate new blood vessel growth. Two endothelial growth factors, VEGF and bFGF, are expressed by many tumors and seem to be among the most important angiogenic stimulators in sustaining tumor growth. The role of angiogenic inhibitors is to keep angiogenic stimulators within their normal range. Inhibitors have half lives which are measured in hours and days, while stimulators' half lives are considerably shorter, most measured in only minutes.

Although first discovered in the late 1960's at Harvard by Dr. Judah Folkman, angiogenesis as a field of knowledge and discovery is still largely dominated by research scientists. Although many physicians and some patients have heard the term angiogenesis, few understand the role of angiogenesis in cancer and numerous other diseases. Peer-reviewed literature documenting the role of angiogenesis in disease and in reversing disease, unless directly tied to an angiogenesis inhibiting pharmaceutical, is customarily not read by most clinicians.

While studies documenting the beneficial effects of less than a dozen angiogenesis inhibiting pharmaceuticals increase in number annually, during the last several decades many peer-reviewed studies have been published which demonstrate how beneficially moderating individual angiogenic inhibitors, through the utilization of natural compounds and other techniques, suppresses disease stimulating angiogenic growth factors. These studies are largely unknown to the practicing medical community. Studies have shown such natural compounds to be safe and effective in the treatment of disease, cost effective, and almost entirely without side effects, and yet most physicians have no knowledge of their well-documented benefit in treatment of disease.

It is estimated that the amount of published literature with respect to the various aspects of medicine, angiogenesis and the diseases it drives doubles every five years. Based solely on the volume of literature, the most advanced treatment options are not always known by practicing clinicians.

For a physician or patient to perform a literature search on the basis of a specific patient sample analysis to determine the full range of peer-reviewed medical articles providing relevant information with respect to the multitude of angiogenic regulators would consume days if not weeks of extensive research. To date, it has not been known to couple the results of an angiogenic diagnostic test with specific peer-reviewed studies providing a range of treatment options to thereby stimulate therapy discussions between physician and patient.

BRIEF SUMMARY OF THE INVENTION

Disclosed is a system and method for targeting relevant research activity for clinical application in response to angiogenic regulator analyses. An angiogenic analysis is performed on a patient blood sample in order to detect the level of each of at least ten angiogenic regulators, in a first embodiment. Alternative embodiments employ the analysis of as few as five angiogenic regulators, and more than ten angiogenic regulators. While individual angiogenic regulators have been correlated with a specific disease state or patient condition by researchers, the present approach precisely measures multiple regulators simultaneously for diagnostic use by a clinician. The levels of the tested regulators are used as indexes to identify relevant peer-reviewed research publications from among a large database of articles. What are believed to be the most relevant peer-reviewed literature reporting research and studies that have been conducted to identify, moderate, and define the mechanisms unique to individual and combinations of angiogenic regulators for various disease states are then provided to the patient and/or to the patient's physician.

In this manner, the vast amount of research-based information is winnowed down to a specifically relevant subset of literature and summarized detail and documents studies for moderating the out-of-range regulator(s) back to within normal or diagnostically relevant ranges. This information in various formats to include lists, charts, spreadsheets, and all other means for organizing detailed, specific and variable information is then made available to the patient or the patient's physician for clinical therapy discussions and analysis. The customized information delivery provides the patient and physician a range of published peer-reviewed therapeutic options and research studies published for moderating each of the out of range regulators to within normal or diagnostically relevant ranges. This unique matching of the literature to a patient's individual chemistry allows the practicing physician a broad range of options that have been evaluated by his peers with which to treat the patient's disease in a highly targeted and unique manner. The report according to the presently described innovation provides the physician with comprehensive research underpinning for the rationale and efficacy for treatment of abnormal regulators by providing the full research documentation, optionally in addition to a summarization thereof for facilitating prescribing detail and dosing.

Preferably, the angiogenic analysis is performed by enzyme-linked immunosorbent assay (ELISA) techniques.

Once the patient sample has been analyzed and levels of certain angiogenic regulators have been obtained, this information is used to intelligently identify what are believed to be the most relevant peer-reviewed research literature pertaining to the respective regulators. The articles or abstracts thereof may be provided to the patient and/or physician in hard copy by mail or courier services, or more preferably in electronic format via email, on a portable memory medium such a DVD or memory stick, or as a communications network address or link to each article or to a set of articles for the respective patient. If only article abstracts or other article identifiers are provided, the patient or physician may choose to obtain the entire article through one of various known literature sources.

Databases of peer-reviewed research studies, such as PUBMED, are well known in the art. In one embodiment of the present system and method, personnel with relevant experience and knowledge in the field of angiogenesis perform an in-depth review of the literature relevant to each of a set of angiogenic regulators. This pool of literature contains at a minimum articles that pertain to the angiogenic regulators tested for in the patient sample analysis. The purpose of this in-depth literature review is to identify a number of research articles that appear to be, at the time of the in-depth review, the most relevant to the respective angiogenic regulator, the relationship between the respective regulator and various diseases and disease states, and to treatment options therefor. In one embodiment, these most-relevant articles represent a preferred set of references that typically form part of the literature identified to the patient and/or physician each time the respective regulator is tested for or more preferably each time the respective regulator is found to have an abnormal or otherwise flagged level in the patient sample.

However, additional patient information is used to further refine the set of literature identified to the patient and/or physician. For example, the patient sample may reflect a specific combination of regulators having respective levels beyond a predetermined normal or diagnostically significant range. Such a combination may be used as the basis for a search engine query of the literature database for the purpose of locating relevant references may not be not part of the preferred set of literature. Since new research is documented at a rapid pace, literature that has been published subsequent to the previously described in-depth review can be discovered via the search engine query.

Additional patient information, such as suspected diagnoses, tumor state and location, family medical history, sex, age, allergies, etc., may also be used to form search engine queries to obtain additional relevant research literature. While it is preferable that algorithms automatically assemble and execute the search engine queries into the literature database, it is expected that manual monitoring and adjustment of the query assembling algorithm will be required for at least an initial time period to optimize the search results. For example, it may be found that search results having a date of publication within a certain period of time are more relevant due to some relatively recent discovery in the field; the search query would thus weight results within this time period more heavily. Manual intervention and monitoring of this search process has the added benefit of enabling the addition of newly found research literature to the preferred set of literature, and possibly the removal or substitution of older or now less favored articles from that preferred set.

Through these techniques, it becomes possible to filter the database contents according to a patient's angiogenic analysis. Only those studies that are relevant to the patient's condition are returned in a professionally informed priority manner.

Research literature relevant to moderation of angiogenic regulators addresses a wide variety of pharmaceuticals, naturally occurring compounds, lifestyle choices (e.g. exercise), and integrative, complementary and alternative therapies that can be employed, much of which may be unknown to clinicians. For example, research has shown that certain pharmaceuticals have off-label applicability to the moderation of angiogenic stimulators. Thalidomide, now prescribed for leprosy and available off-label, is currently being used in clinical trials as a blocker of angiogenic growth factors (bFGF, VEGF, TNF-alpha). AVASTIN (Genentech, Inc.), currently prescribed for colorectal cancer, can be applied to the treatment of other cancers. Captopril, a high blood pressure medication, also has anti-angiogenic properties. Copper chelators such as zinc have been reported to impact angiogenesis regulators.

Studies have shown that numerous non-toxic compounds, in large measure spices, have beneficial impact on boosting inhibitors and repressing stimulators. For example, antioxidant N-acetyl-cysteine (NAC), which is available as an over-the-counter supplement, has been shown to create endothelial cell apoptosis and reduction of microvascular density within the core of the tumor. Further, curcumin has been identified as a substance that suppresses TNF-alpha, IL-1, and IL-6 angiogenesis activators. In addition, studies may also indicate that certain lifestyle changes may be beneficial, including yoga, diet, sleep patterns, meditation and exercise.

The specific utility of the disclosed system and method lies in allowing clinicians and their patients to take advantage of the most advanced research for the specific determinants of the process (angiogenesis) which underlies the individual patient's disease.

BRIEF DESCRIPTION OF THE SEVERAL VIEWS OF THE DRAWINGS

Other features and advantages of the present invention will be apparent from the following detailed description of the invention, taken in conjunction with the accompanying drawings of which.

DETAILED DESCRIPTION OF THE INVENTION

The present invention pertains to systems and methods for targeting and summarizing relevant research activity in response to the analysis of angiogenic regulators in a biological sample. Preferably, the angiogenic analysis is performed on a blood sample from a patient. In a first embodiment of the present invention, the level of each of at least ten angiogenic regulators is measured. Alternative embodiments employ the analysis of as few as five angiogenic regulators, and more than ten angiogenic regulators. Peer-reviewed research publications that pertain to the field of diagnosing and treating cancer and other diseases driven by imbalances in angiogenic regulators are indexed according to the respective regulators studied therein. The measured angiogenic regulator levels are then used by a data processing unit to identify research studies that pertain to the moderation of the same subset of regulators. The identified research is then summarized and provided to the patient and/or to the patient's treating physician.

The blood sample can be drawn in any conventional manner. With respect to FIG. 1, the angiogenic analyzer 102 comprises test reagents and related equipment and is preferably performed using ELISA technology using sample processing, liquid handling and enzyme reading equipment. As is known, ELISA is a single-plex technology, meaning that for a given sample volume, only a single antigen can be quantitated at a time. This assay is based upon the specific recognition of the antigen of interest by antibodies that are bound to the surface of a micro titer well. These plate-bound antibodies capture their cognate antigen from complex biological samples. The resulting antigen-antibody complex is then detected by an enzyme-labeled antibody specific for the same antigen. Upon addition of the appropriate substrate, the enzyme produces a colorimetric reaction within the micro titer well in which the color density is directly proportional to the concentration of the protein within the sample. The Tecan FREEDOM EVOLYZER (Tecan Trading AG) is capable of fully automated ELISA processing and could be employed in the presently disclosed system and method.

Figure 1:
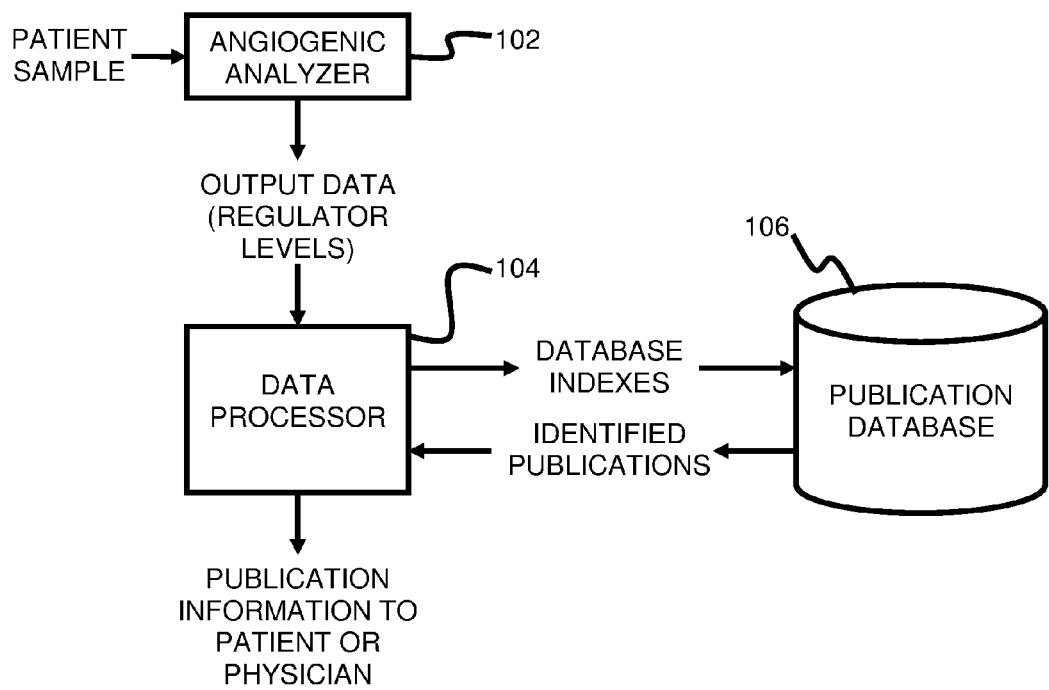
FIG. 1 illustrates schematically a preferred system for targeting relevant research activity in response to angiogenic regulator analyses according to the present invention.

Alternative embodiments of the present invention employ planar microarray technology or bead-based assays within the functional block labeled "angiogenic analyzer 102" in FIG. 1. The analysis can also be performed by magnetic particle assays like the Siemens Centaur system, fluorescent bead technology like the LUMINEX system (Luminex Corporation), chemiluminescence immunoassay technology like the Abbott Prism immunoassay analyzer, etc.

In a preferred embodiment, the panel of angiogenic regulators that are tested in the angiogenic analyzer 102 include VEGF, EGF, bFGF-basic, IL-2, PDGF-BB but which may also include TNF-alpha, IL-1Beta, IL-8, IL-10, TSP-1, COX-2, HGF, IGF-1, MMP-2, MMP-9, TNF-Beta, TGF-Beta, Angiogenin, GM-CSF, Endostatin, Angiostatin, IL-6, G-CSF, IL-7, Angiopoitin-1 and all other angiogenesis growth factors, stimulators or endogenous inhibitors.

The results of the regulator level analysis are stored in internal memory of the analyzer 102 and in a first embodiment are output in digital format to a portable data medium such as a DVD, memory stick, etc. Alternatively, the regulator level analysis is transmitted from the analyzer as a sequence of electromagnetic signals over a transmission medium such as an electrically conductive or optical transmission line or over a wireless transmission medium via RF, IR or any other practical transmission means. In a further embodiment, the regulator level analysis is output in printed (i.e., alphanumeric and/or graphical) form.

The measured regulator levels are provided to a data processing unit 104, also referred to herein as a data processor, via portable data medium interface such as a DVD reader, memory stick slot, etc., wireless or wired receiver, or keyboard, mouse, or touch-sensitive display screen in combination with a graphical user interface (GUI). Other conventional means for data input are used in further embodiments. The data processing unit implementing the methods of the present invention can be a standard personal computer, for example based upon an Intel or other microprocessor, including standard memory, disk drives and/or optical storage, data input/output facilities, network/communications interfaces, etc. Alternatively, the data processing unit may be provided as a customized data processor, especially configured to receive the output of the angiogenic analyzer and to use those data values in parsing a literature database, as discussed in more detail below.

In a further embodiment, the angiogenic analyzer 102 and the data processor 104 may be provided within the same physical enclosure and therefore the distinction between the two would be functional rather than physical.

The data processor 104 is in communication with a publication database 106 which contains a large number of peer-reviewed research studies and publications, each of which in some fashion correlates the levels of certain angiogenic regulators with a disease, a disease stage, a technique for moderating an imbalance among the respective angiogenic regulators discussed therein to thereby treat or inhibit the growth of a disease or afflicting condition, modify angiogenesis regulators in general, or in a prevention of disease capacity, etc. For example, in a preferred embodiment, the publication database is the well-known PUBMED database, and the data processing unit is in communication therewith via a communications network such as the Internet.

In one embodiment, the publication database is parsed in order to identify each publication that pertains in a meaningful way with an angiogenic regulator that is tested for by the angiogenic analyzer 102. A person or persons skilled in the art of angiogenesis and its role in cancer and other diseases reviews the results to identify a subset of publications that appear to be most relevant to one or more of disease diagnosis, treatment, angiogenic moderation, etc. This subset forms a preferred set of literature that is typically summarized and reported to a patient and/or physician at least when the level of the respective regulator is beyond a normal or diagnostically significant range.

Thus, if ten angiogenic regulators are included in the test panel performed by the angiogenic analyzer 102, the publication results provided to the patient and/or physician will include at least the preferred set of publications for each of the regulators in the patient sample that were found to have a level beyond a respective normal or diagnostically significant range. In a further embodiment, the preferred set of publications for all of the regulators in the patient sample that were tested in the analyzer are provided. Ideally, the steps involved in identifying the preferred set of literature for each regulator are repeated at periodic intervals in order to ensure the latest relevant literature is included and added to the summary document.

Preferably, the system and method of the present invention further includes the performance of an automated search on the basis of one or more of: the angiogenic regulators in the patient sample that were tested and found to have a level beyond a predetermined normal or diagnostically significant range; all of the angiogenic regulators tested by the analyzer; an actual patient disease diagnosis; a suspected patient disease diagnosis; a patient's family medical history; other characteristics of the patient's health including other diseases or conditions, allergies, etc. Literature from the database of peer-reviewed articles may be weighted by the query according to the date of publication—more recent publications may take precedence over later published studies. The results from the search query augment the relevant preferred set(s) of literature and summary treatment recommendations to be provided to the patient and/or physician.

It is recognized that such a query system, in order to be eventually automated, must be monitored and optimized by personnel skilled in the art of angiogenesis research. During this learning period, the results of the query are monitored to assure that the most relevant literature is being returned and, if not, the content of the queries (i.e., how the queries are constructed) is modified. It is intended that the combination of the preferred set(s) of literature and the query results will ultimately provide the patient and/or physician with the most relevant and current research on angiogenic modulation, along with information in a summarized format on disease treatment and prevention.

The database 106 is a computer-readable memory configured with data for the practice of the methods of the present invention. The database can include main, or dynamic, memory that is directly accessible to a processor 104 and configured with publication data. It can also include optical, magnetic, fixed or removable media configured with publication and indexing data. The database may be hosted in a separate physical enclosure or may be provided on a memory facility associated with the data processor. It can also include a subscription-based, third-party hosted database accessible by a communications network such as the Internet.

The data processor 104 uses the output data from the angiogenic analyzer as part of a search query into the publication database 106. Specifically, the data processor may be programmed with an identification of the preferred set of literature for each of the relevant angiogenic regulators. This identification may be a pointer or address of a database entry, identification information that is adequate to allow the data processor to look up an article or research paper in the database, or an abstract of each of the documents making up the respective preferred set.

Alternatively, the sets of preferred literature may be stored in the publication database 106. In this case, the data processor uses the regulator levels from the angiogenic analyzer 102 as indexes into the database to retrieve the preferred set(s) of literature as the "identified publications," as illustrated in FIG. 1. In addition, as discussed above, the data processor performs one or more queries into the publication database on the basis of subsequent information provided by the patient or the patient's physician. The substance of this additional information is discussed more fully below.

Preferably, the relevant peer-reviewed research studies are each correlated with a potential treatment option, which may include specific pharmaceutical therapies, chemotherapies, specific naturally occurring compound therapies, diet programs, exercise programs, or meditation-based therapies, all of which may be provided directly and/or in a summary format. Further, the relevant research studies are preferably pertinent to angiogenesis modulation.

The matched research studies are then made available to the patient and/or the patient's physician so that the various techniques disclosed in the studies for regulator moderation can be reviewed and discussed between the patient and physician for therapy planning and treatment decisions. This is of particular importance in the case of certain rapidly advancing diseases. The matched studies may be provided on a removable data carrier such as a DVD or memory stick, or as electronic data files that are stored at an addressable memory location on a communications network such as the World Wide Web or that are communicated to the patient or physician via electronic communications such as email. In any case, either the publication itself or a synopsis or abstract thereof may be provided as the output to the patient or physician.

The methods of the invention are implemented by computer program instructions which have been loaded into memory associated with the data processor 104. The program and the computer instructions comprising it can be introduced into the data processor then loaded into internal memory in any convenient manner, for example, by being read from removable optical or magnetic storage media on which it is recorded, or by being transmitted over network connections, etc. Once so introduced, the program instructions reside in the permanent storage of the data processor 104 until needed, whereupon they are loaded into dynamic memory accessible to the processor and cause the processor to perform the methods of the present invention.

The data processor 104 may be configured with such security measures as are known in the art to protect the privacy of individual patients as may be required by applicable regulations.

Figure 2:
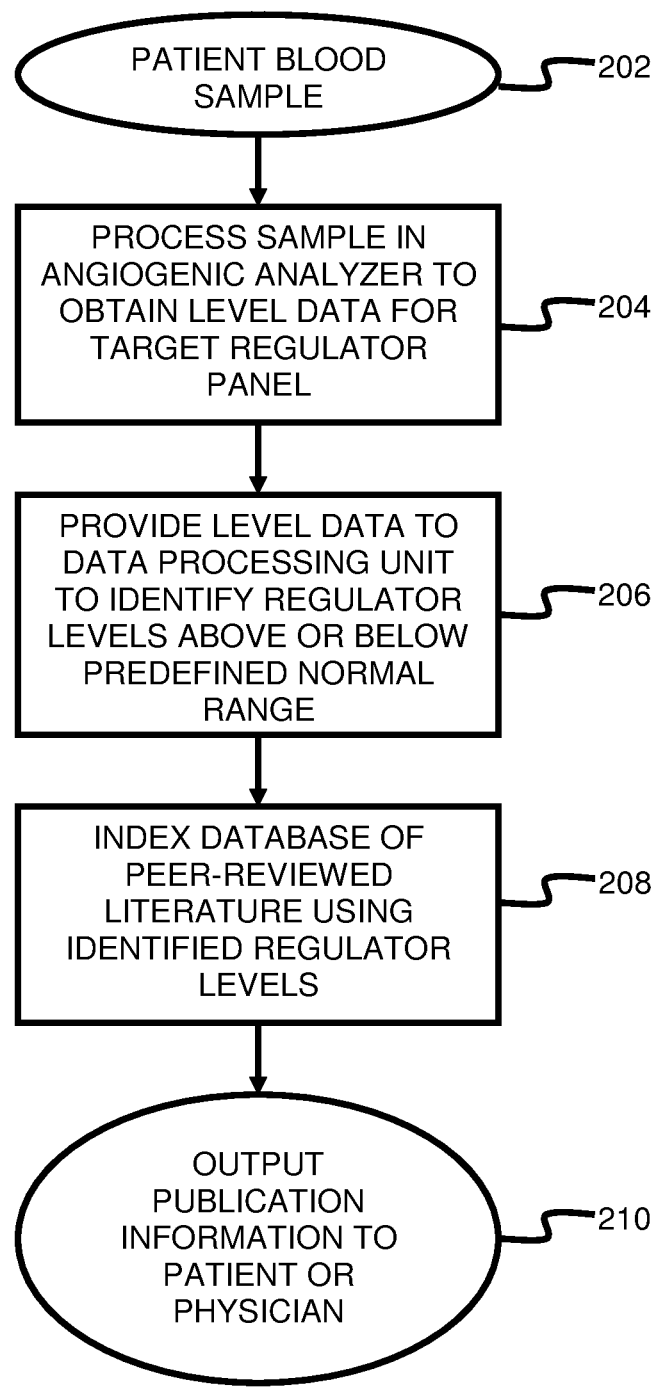
FIG. 2 illustrates a preferred implementation of the general method of targeting relevant research activity in response to angiogenic regulator analyses according to the present invention.

With regard to FIG. 2, a preferred method of practicing the present invention is disclosed. First, a patient blood sample is obtained 202 through techniques known in the art. The sample is then provided to an immunochemistry analyzer to obtain the level data for at least ten target angiogenic regulators (also referred to as a target regulator panel) 204. Again, this is but one embodiment of the presently disclosed invention. Alternatives employ as few as five and more than ten target regulators. The type of equipment that can be employed to carry out this step is described in greater detail in the foregoing.

Once the level for each of the relevant angiogenic regulators has been determined, they are provided to a data processing unit which can identify those regulators, either stimulators or inhibitors, having a respective level that is above or below a predetermined normal range or other diagnostically determined range 206. The data processor then uses all of the measured regulator level data, or alternatively just those regulator levels outside the respective normal range or determined range, as indexes into a database of peer-reviewed literature 208. Such literature has been preprocessed to identify the respective angiogenic regulators relevant thereto as well as the level ranges considered therein, all as discussed above. As in the foregoing, at least the preferred sets of literature (or identifiers thereof such as abstracts) for each of the tested regulators having abnormal or other diagnostically significant level values, and optionally for all of the tested regulators, are output to the patient and/or physician. Also as in the foregoing, this information may be augmented by the results of one or more queries performed by the data processor 104 on the contents of the publication database 106 using information obtained from the patient and/or physician. The latter concept is further discussed in the context of FIG. 3, below.

Finally, the research studies that correlate to the patient regulators, level data, and optionally other patient data are output to the respective patient and/or his/her physician 210. This step may take many forms. For example, the recipient may be provided with an email including an electronic copy of each relevant study or an abstract thereof. Alternatively, the recipient may receive an email with network addresses, such as hypertext transfer protocol (HTTP) universal resource locators (URLs), that link to the relevant studies, or to abstracts thereof. Accompanying the identified publications, in a preferred embodiment, is a report of the patient angiogenic regulator test results, optionally combined with a listing of the respective normal or diagnostically significant ranges. A summary of the additional patient information upon which the database was queried is also provided in an alternative embodiment.

Figure 3:
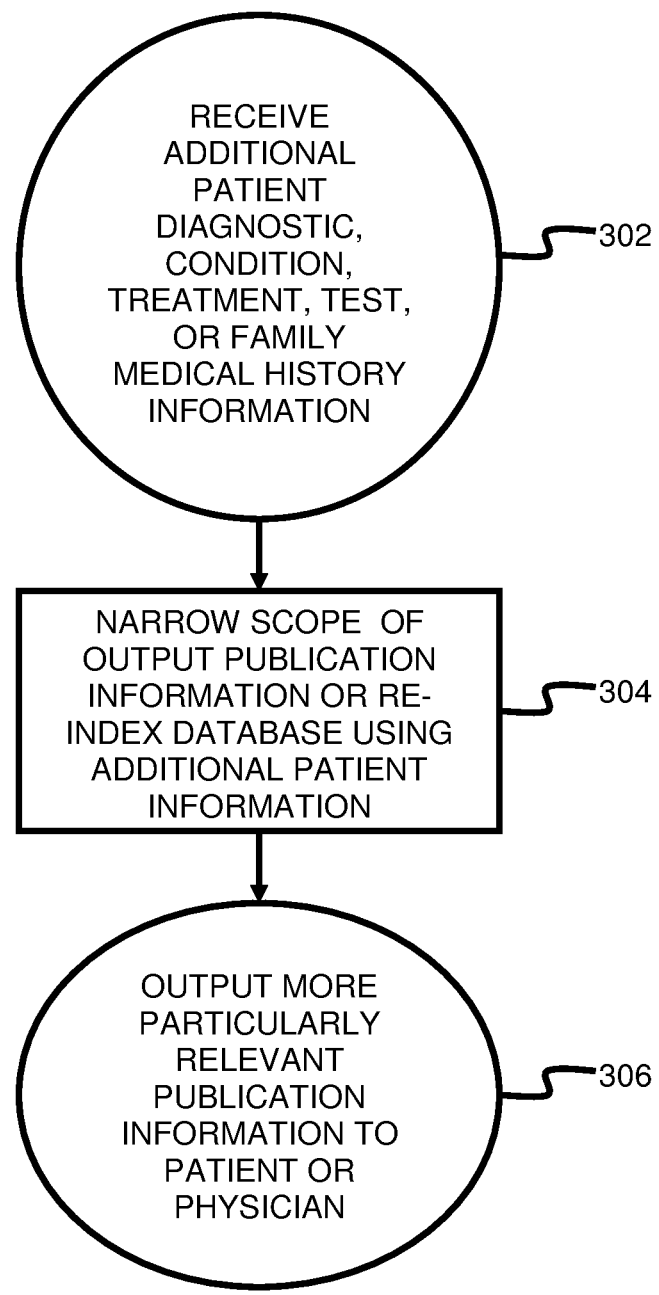
FIG. 3 illustrates a further refinement of the method of FIG. 2.

With regard to FIG. 3, and as previously alluded to, a further embodiment of the presently disclosed system and method includes the ability to refine the set of peer-reviewed literature returned to the patient and/or clinician. Specifically, the data processor 104 is configured to receive additional data regarding the patient. This information may include a diagnosis or suspected diagnosis of a particular condition or disease or the determined stage of a disease, treatment that the patient has in the past undergone or is currently undergoing, other radiologic or biologic test results (such as Positron Emission Tomography (PET) scan Standardized Uptake Value (SUV) scores), a patient's mitotic count, current and prior medicines prescribed to the patient, patient allergies, and relevant aspects of the patient's family medical history, among other factors. The provision of this information may be prompted by the data processor 104 providing an on-line survey to the patient or to the patient's physician, whereby the respondent (the patient and/or physician) goes through a series of inquiries requesting the additional information. The inquiries may ask for size and quantity of tumors, primary tumor site, time frame since last scan, and other assorted information. Alternatively, the respondent may choose from a list of additional information that is useful to be provided. In another embodiment, the system of FIG. 1 and the method of FIG. 2 include a service representative who asks the respondent for the additional information and who inputs this information to the data processor.

Once the additional information has been provided, the data processor uses customized algorithms or artificial intelligence to parse the data on the basis of key words or via pattern matching. The additional information is then used to form queries that are input to a search engine operating on the content of the publication database 106. The output literature may be organized according to publication date, whether each pertains to treatment versus diagnosis, relevance on the basis of the number of angiogenic regulators considered therein that are in common with those of the patient sample having abnormal levels, etc. This enables the more rapid identification of potentially relevant studies by the patient and/or physician.

In yet a further embodiment, the system and method of the present invention provides a feedback path from the patient and/or physician so that individual results can be graded or otherwise scored as to their relevance to the patient's situation. Such feedback can for instance be used to adjust the content of the preferred set of literature for one or more regulators, or to fine tune the query process that employs patient-specific information as input and adjust summary recommendations from the content of the preferred set of literature.

By connecting research dots (i.e., peer-reviewed studies) to a patient's unique chemistry, it is intended to provide the physician and the patient peer-reviewed research with summary treatment recommendation to discuss angiogenesis therapy options. For many diseases driven by angiogenesis, of which cancer and coronary artery disease are two examples, time is often critical to the survival of the patient. The invention's usefulness is that precious time is saved in the treatment of disease by allowing the clinician to precisely target the underlying drivers of the patient's disease on the basis of the most current research treatment.

Many changes in the details, materials, and arrangement of parts and steps, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

What is claimed is:

1. A system for targeting relevant research activity in response to angiogenic regulator analyses, comprising:
   an angiogenic analyzer for receiving at least one patient blood sample, for measuring in a single patient blood sample the level of each of at least ten angiogenic regulators, and for generating a data output indicative of the respective level of each of the at least ten measured angiogenic regulators;
   a database unit comprising plural entries, each entry corresponding to a respective publication and indexed at least according to a range of levels for each of at least one angiogenic regulator; and
   a data processing unit in communication with the angiogenic analyzer and the database unit for receiving the data output from the angiogenic analyzer, for identifying entries in the database unit for which one or more of the patient angiogenic regulator levels are addressed therein, and for providing an identification of the identified database entries.

2. The system of claim 1, wherein the at least ten angiogenic regulators are selected from the group consisting of Vascular Endothelial Growth Factor, Epidermal Growth Factor, Fibroblast Growth Factor-Basic, Interleukin-2, Platelet-derived Growth Factor-BB, Tumor Necrosis Factor-alpha, Interleukin-1 beta, Interleukin-8, Interleukin-10, Thrombospondin-1, Cyclooxygenase, Hepatocyte Growth Factor, Insulin like Growth Factor, Matrix Metalloproteinase-2, Matrix Metalloproteinase-9, Tumor Necrosis Factor-beta, Transforming Growth Factor-beta, Angiogenin, Granulocyte Macrophage Colony-Stimulating Factor, Endostatin (collagen XVIII fragment), Angiostatin (plasminogen fragment), Interleukin-6, Granulocyte Colony-Stimulating Factor, Interleukin-7, Kringle 5 (plasminogen fragment), Angiopoitin-1, and Fibrinogen.

3. The system of claim 1, wherein the data output is provided on a removable data carrier.

4. The system of claim 1, wherein the data output is received by the data processing unit as a sequence of electromagnetic signals transmitted over a transmission medium.

5. The system of claim 1, wherein the database unit and the data processing element are integrated within a common physical enclosure.

6. The system of claim 1, wherein the angiogenic analyzer measures the level of each of the at least ten angiogenic regulators via a technique selected from the group consisting of enzyme-linked immunosorbent assay (ELISA), planar microarray, bead-based assays, magnetic particle assays, and chemiluminescence immunoassays.

7. The system of claim 1, wherein the database unit further comprises, in conjunction with each of the plural entries, the text, data and images, as such exist, of the respective publication.

8. The system of claim 7, wherein the data processing unit is further for providing, in conjunction with the identification of the identified database entries, the text, data and images, as such exist, of each of the respective publications.

9. The system of claim 1, wherein each identification of the identified database entries is provided as an address of the respective publication in a database of publications accessible by a communications network.

10. The system of claim 1, wherein each publication is a peer-reviewed research study from which the levels of at least one angiogenic regulator is correlated with a recommended treatment option.

11. The system of claim 10, wherein the recommended treatment regime is selected from the group consisting of specific pharmaceutical, chemo- or radiation therapies, specific naturally occurring compound therapies, diet programs, exercise programs, meditation-based therapies, and integrative, complementary, and alternative therapies.

12. The system of claim 10, wherein the recommended treatment regime is for the purpose of angiogenesis inhibition.

13. The system of claim 1, wherein the data processing unit is further for providing the indication of the identified database entries to the patient from whom the blood sample was obtained or to a physician caring for the patient.

14. The system of claim 1, wherein the data processing unit is further for receiving from the patient from whom the blood sample was drawn, or a physician caring for the patient, additional information and for identifying from among the database unit entries for which the patient additional information is relevant.

15. The system of claim 14, wherein the additional information is selected from the group consisting of a diagnosed patient condition, a suspected patient condition, a diagnosed disease stage, mitotic count, radiologic or biologic test results, current and prior medications prescribed, allergies, and family medical history.

16. The system of claim 1, wherein the data processing unit is further for extracting treatment recommendations from the identified database entries and for providing a summarization of the treatment recommendations in conjunction with the identification of the identified database entries.

17. A method of targeting relevant research activity in response to angiogenic regulator analyses, comprising:
providing a patient blood sample to an angiogenic analyzer;
measuring the level of each of at least ten angiogenic regulators in the blood sample;
generating a data output indicative of the respective level of each of the at least ten measured angiogenic regulators;
providing a database unit comprising plural entries, each entry corresponding to a respective publication and indexed at least according to a range of levels for each of at least one angiogenic regulator;
identifying, with a data processor, each entry in the database unit for which the patient angiogenic regulator levels in the data output are within the respective ranges of levels; and
providing an identification of the identified database entries.

18. The method of claim 17, wherein the at least ten angiogenic regulators are selected from the group consisting of Vascular Endothelial Growth Factor, Epidermal Growth Factor, Fibroblast Growth Factor-Basic, Interleukin-2, Platelet-derived Growth Factor-BB, Tumor Necrosis Factor-alpha, Interleukin-1 beta, Interleukin-8, Interleukin-10, Thrombospondin-1, Cyclooxygenase, Hepatocyte Growth Factor, Insulin like Growth Factor, Matrix Metalloproteinase-2, Matrix Metalloproteinase-9, Tumor Necrosis Factor-beta, Transforming Growth Factor-beta, Angiogenin, Granulocyte Macrophage Colony-Stimulating Factor, Endostatin (collagen XVIII fragment), Angiostatin (plasminogen fragment), Interleukin-6, Granulocyte Colony-Stimulating Factor, Interleukin-7, Kringle 5 (plasminogen fragment), Angiopoitin-1, and Fibrinogen.

19. The method of claim 17, wherein the data output is generated by the angiogenic analyzer on a removable data carrier.

20. The method of claim 17, wherein the data output is generated by the angiogenic analyzer and received by the data processor as a sequence of electromagnetic signals transmitted over a transmission medium.

21. The method of claim 17, wherein the database unit and the data processor are provided as an integrated device.

22. The method of claim 17, wherein the angiogenic analyzer measures the level of each of the at least ten angiogenic regulators via a technique selected from the group consisting of enzyme-linked immunosorbent assay (ELISA), planar microarray, bead-based assays, magnetic particle assays, and chemiluminescence immunoassays.

23. The method of claim 17, wherein the database unit is provided, in conjunction with each of the plural entries, the text, data and images, as such exist, of the respective publication.

24. The method of claim 23, wherein the database unit is further for providing, in conjunction with the identification of the identified database entries, the text, data and images, as such exist, of each of the respective publications.

25. The method of claim 17, wherein the database unit is further for providing, in conjunction with each of the plural entries, an address of the respective publication in a database of publications accessible by a communications network.

26. The method of claim 17, wherein the database unit is further for corresponding each of the plural entries with a respective peer-reviewed research study from which levels of at least one angiogenic regulator is correlated with a recommended treatment option.

27. The method of claim 26, wherein the recommended treatment regime is selected from the group consisting of specific pharmaceutical, chemo- or radiation therapies, specific naturally occurring compound therapies, diet programs, exercise programs, meditation-based therapies, and integrative, complementary, and alternative therapies.

28. The method of claim 17, wherein the recommended treatment regime is for the purpose of angiogenesis inhibition.

29. The method of claim 17, further comprising providing the indication of the identified database entries to the patient from whom the blood sample was obtained or to a physician caring for the patient.

30. The method of claim 17, further comprising receiving from the patient from whom the blood sample was drawn, or a physician caring for the patient, additional information in the data processor and identifying from among the identified database unit entries for which the patient additional information is relevant.

31. The method of claim 30, wherein the additional information is selected from the group consisting of a diagnosed patient condition, a suspected patient condition, a diagnosed disease stage, mitotic count, radiologic or biologic test results, current and prior medications prescribed, allergies, and family medical history.

32. The method of claim 17, further comprising extracting treatment recommendations from the identified database entries and providing a summarization of the treatment recommendations in conjunction with the identification of the identified database entries.

* * * * *